United States Patent [19]

St. Pierre et al.

[11] Patent Number: 5,856,308
[45] Date of Patent: Jan. 5, 1999

[54] ARTIFICIAL COLLAGEN

[75] Inventors: Serge St. Pierre, Ile Bizard; Teresa Brodniewicz, Pointe-Claire, both of Canada

[73] Assignee: Haemacure Corporation, Quebec, Canada

[21] Appl. No.: 721,434

[22] Filed: Sep. 27, 1996

[51] Int. Cl.$^6$ ..................................................... A61K 38/39
[52] U.S. Cl. .......................... 514/18; 106/160.1; 530/356
[58] Field of Search ........................... 514/18; 106/160.1; 530/356

[56] References Cited

U.S. PATENT DOCUMENTS

| | | |
|---|---|---|
| 4,585,585 | 4/1986 | Waite . |
| 5,209,776 | 5/1993 | Bass et al. . |
| 5,290,552 | 3/1994 | Sierra et al. . |
| 5,405,757 | 4/1995 | Prockop et al. . |
| 5,412,076 | 5/1995 | Gagnieu . |
| 5,413,791 | 5/1995 | Rhee et al. . |
| 5,446,091 | 8/1995 | Rhee et al. . |
| 5,475,052 | 12/1995 | Rhee et al. . |
| 5,476,666 | 12/1995 | Rhee et al. . |

FOREIGN PATENT DOCUMENTS

WO 97/19106   4/1997   WIPO .

OTHER PUBLICATIONS

Fields et al., "Three Dimensional Orthogonal Solid–Phase Synthesis of Cell–Adhesive, Triple Helical Collagen Peptides", Peptide Chem. (1992) pp. 14–18.

*Primary Examiner*—Cecilia J. Tsang
*Assistant Examiner*—Patrick R. Delaney
*Attorney, Agent, or Firm*—Hoffman, Wasson & Gitler

[57] ABSTRACT

The invention provides artificial collagen comprising a stabilized ordered triple helix of copolypeptide strands containing repeating amino acid triads. The collagen may be modified with groups which improve its physical or chemical properties for the intended use, such as adhesive and cross-linking groups. Artificial collagen according to the invention is particularly useful as a wound closer and healer.

35 Claims, No Drawings

ARTIFICIAL COLLAGEN

BACKGROUND OF THE INVENTION

1. Field of the Invention

The invention pertains to artificial collagen oligopeptides and related compounds useful in clinical (including veterinary) applications.

Proteins and oligopeptide fragments thereof derived from animal sources have numerous well-known clinical uses. Collagen in particular is useful in the production of matrices for the support of various types of cells to promote the regeneration of damaged tissue such as nerve, bone, skin, or vascular tissues, and as a component of fibrin sealants. Typically, clinical grade commercial proteins such as collagen are isolated from their mammalian source, purified and sterilized to the extent feasible without denaturing the molecule, and, often, chemically modified to specialized use.

While natural collagen has many clinical advantages for such applications, including biocompatibility, shapability, and hemostatic properties, the use of mammal (including human- and bovine-)derived collagen presents potential hazards, especially the transmission of infectious agents from donor to donee. For example, the safety of collagen of animal origin has recently been placed in doubt with the recognition of the prevalence in Europe of bovine spongious encephalitis. This disease of unclear causes is of great concern for collagen users, since most of commercial collagen is of bovine origin and efficacy of conventional purification and sterilization procedures against the causative pathogen(s) is presently purely hypothetical. Further, the use of collagen of human origin has not obviated problems of possible contagion. Even though collagen purification methods currently in use appear to effectively eliminate viruses and retroviruses present, the possibility of the presence of other infectious agents unsusceptible to such treatment, such as proteins the size of collagen, lurks in the background.

It is accordingly desirable to provide a simplified oligopeptide structure having collagen-like properties for similar clinical applications, which can be readily manufactured in commercial quantities to obtain a substantially pure product, free of contaminants potentially dangerous to the recipient.

2. Description of Related Art a) Collagen-like substances

Studies on the primary structure of collagen performed more than 20 years ago (Treatise on Collagen, volume 1; Ramachandran, ed., Academic Press, London, pp. 441–526, 1967; Protein Chem. 25:243–352, 1971) revealed the presence of glycine (Gly) as every third residue in a peptide chain, and a high proportion of the imino acid residues proline (pro) and hydroxyproline (Hyp) as characteristic of natural collagen from various mammalian species, including man (Biochem. 5:3803, 1966; Biochem. 10:2076, 1971). The studies also demonstrated that collagen contains a large number of tripeptide sequences of the form of Pro-Hyp-Gly, Pro-X-Gly, or X-Hyp-Gly, where X is an amino acid residue other than Pro, Gly, or Hyp. Numerous subsequent sequence studies have shown that Hyp mainly occurs as Y in the collagen repeating unit $(X-Y-Gly)_n$. Hyp is synthesized in vivo during the post-translational modification of collagen by the enzymatic hydroxylation of Pro after its incorporation into the polypeptide sequence, a critical step in the synthesis of collagen, since unhydroxylated collagen is not efficiently secreted from cells, has a lower denaturation temperature than fully hydroxylated collagen, and is therefore susceptible to nonspecific proteolysis. An examination of the primary structure of the α-chains of mammalian collagen reports that in triads of the type Gly-Pro-X and X-Pro-Gly, only the latter are hydroxylated (Biochemistry of Collagen, Ramachandran et al. eds, Plenum Press, New York, N.Y. p. 1, 1976). Further, polytripeptides in which X=Pro were the most efficient substrates for the hydroxylation, whereas increasing complexity of the side chain of other residues at X decreased the efficiency with which hydroxylation occurred (Biochem. 17:2892. 1978).

Early molecular models of collagen, comprising three peptide chains containing the above tripeptides, showed the chains twisted in a gradual right-handed helix, with each chain in the helix locked into a left-handed helix of poly-Pro II type by a large number of imino acid residues (Biochem. Biophys. Acta 109:314, 1965). In attempts to clarify the correlation between the primary and secondary structures of collagen, a variety of polypeptides with repeating sequences (Pro-Pro-Gly), (Pro-Hyp-Gly), and others have been synthesized and evaluated during the past twenty years. It was found that those sequences form highly stable triple-helical structures isomorphic to those of natural collagen, both in the solid state (J. Mol. Biol. 65:371, 1972). Studies have proposed that Hyp considerably stabilizes the collagen triple helix and contributes to the tertiary and quaternary structures of the protein by participating in intra- and intermolecular hydrogen bonding (Biochem. Biophys. Acta 322:166, 1972; Curr. Sci. 44:1, 1975).

Pioneering work on synthetic collagen models has also been done with polydisperse mixtures of sequential polytripeptides containing Pro and Gly (J. Mol. Biol. 43:461, 1969). Monodisperse oligotripeptides of $(Pro-Pro-Gly)_n$ or $(Pro-Hyp-Gly)_n$ sequences, where n=2–10, have also been prepared, with X-ray diffraction patterns of the former, wherein n was 4 or greater showing collagen-like diffraction patterns. Circular dichroism spectra of penta- and octadecapeptide films cast from solution are consistent with the conformation of collagen (Biopolymers 17:1215, 1978).

Notwithstanding the above described studies on the physical and biochemical characteristics of collagen and related proteins as well as numerous additional studies, little has been published firmly correlating these findings with properties of collagen which makes this protein clinically useful. One such property is that a great variety of cells, including epithelial cells, fibroblasts, platelets, and keratinocytes adhere to and migrate on specific regions within the triple-helical domain of types I, III and IV collagen; it has been recently reported (J. Biol. Chem. 265:14153, 1993) that triple helicity, more than the primary structure of the collagen peptide chains, is required for cell adhesion to and spreading on a specific collagen sequence, as the tested cells spread upon and adhered to the helical structure, while the single-stranded corresponding sequence was inactive in this regard (Biopolymers 33:1695, 1993).

Recently, it has been shown that bringing three (Pro-Hyp-Gly), chains in register by means of a template can significantly improve stability of the triple helix. The template approach has been reported previously, where the templates utilized are either 1,2,3-propanetricarboxylic acid (Biopolymers 18:2359, 1979), a lysine-lysine dimer (J. Theor. Biol. 153:585, 1991; Biopolymers 33: 1695–1707, Letters 334:272, 1993; Biopolymers 27:157, 1988; Biopolymers 19:1909, 1980; FEBS Letters 334:272, 1993; Biopolymers 25:1081, 1986) or Kemp triacid (cis,cis-1,3,5-trimethylcyclohexane-1,3,5-tricarboxylic acid or KTA) (J. Am. Chem. Soc. 118:5156, 1996).

Each of the above-cited publications is incorporated herein by reference.

b) Polyethylene glycol

Polyethylene glycol (PEG) has been used as a protein modifier for the past twenty-five years. It has been used to react with free amino groups on proteins, using various activated PEGs, such as activated monomethoxypolyethylene glycol. Covalently linked to clinically useful proteins, it can improve their performance and safeness for therapeutic use. It was shown to decrease antigenicity of bovine serum albumin (BSA) (J. Biol. Chem. 252:3578, 1977) and to improve plasma half-life of the native protein by increasing its resistance to proteolytic enzymes (J. Biol. Chem. 252:3578, 1977). It also increases hydrophilicity at the surface of the modified protein (Biotechnol. Appl. Biochem. 17:115, 1993). PEG is recognized as safe for subcutaneous and oral uses in humans and in animals.

SUMMARY OF THE DISCLOSURE

The invention provides artificial collagen having biomechanical and biological properties similar to those of native collagen. Like native collagen, the compounds of the invention are biocompatible, but are of a simplified oligopeptide structure which can be easily synthesized in laboratory or commercial quantities; the compounds, herein also referred to as "collagen mimics", can also be genetically engineered as fusion proteins/polypeptides employing techniques well-known in the art. Compounds so manufactured are free to contaminants frequently associated with purified native collagen products, particularly mammalian pathogens. Further, the core oligopeptide structure is easily modified to provide collagen mimics having biomechanical and/or biological properties particularly suited for their intended use, as by varying the molecular weight of the mimic, by apt selection and sequencing of core amino acid residues, or by covalent linking of selected modifying groups to specific amino acid functional groups. For in vivo use, potential immunogenicity of the mimics is easily minimized, as by minimizing or masking charged residues, as known in the art.

Collagen mimics according to the invention are particularly suitable for use in wound healing or closing, in plastic or reconstructive surgery, and similar applications as known for native collagen. The mimics may be used alone or combined with other biomaterials such as fibrin for use, for example, as connective matrices to improve adherence of fibrin sealants for wound closing and healing, as biodegradable supports for skin cell cultures used to prepare artificial skin for the treatment of skin wounds, as biomaterials for use in place of bovine collagen in plastic surgery, or alone as wound sealants.

DETAILED DESCRIPTION OF THE INVENTION

1. Collagen Mimics

The collagen mimics of the invention are characterized by a core comprising an ordered triple helix of at least three copolypeptide strands of repeating amino acid triads ($X_{aa}$-$X_{bb}$-Gly), each strand being linked at the C-terminal end thereof to a common template for stabilization of the helical secondary structure. The strands may be interwoven or braided, and are each optionally spaced from the template by a bifunctional spacer molecule covalently linked between the C-terminal end of the strand and the template. For optimum stability of the helix, the strands are substantially identical.

The collagen mimic core may be modified by an adhesive moiety (AM) covalently bonded to the template, containing active groups for promoting cohesion of the mimic structure or adhesion of the mimic to dissimilar materials such as skin cells or tissues.

The core may also be modified by a polymer for altering the biophysical or biochemical properties of the mimic, covalently linked to the distal end of one or more of the peptide strands or adhesive moiety, or to functional groups on the strand or adhesive moiety backbones, or to the template.

The artificial collagen of the invention is a water-soluble and ordered, stabilized copolypeptide triple helix of the following formula A:

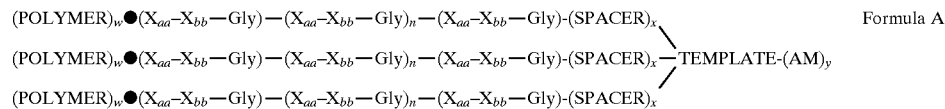

Formula A

Wherein:

n is from about 1 to 28;

x is one or zero;

y is one or zero;

w is from 0 to about 30 and at least one of x, y or w is one or more.

Herein, the IUPAC three-letter notation system for amino acids (IUPAC-IUB Commission on Biochemical Nomenclature, Eus. J Biochem. 1:375, 1967) is followed.

The mimic core consists essentially of a primary structure of three strands of repeating amino acid triads ($X_{aa}X_{bb}$Gly)$_{n+2}$ in a secondary triple helical structure preferably stabilized by a template. In each triad, $X_{aa}$ and $X_{bb}$ are each independently hydrophilic or neutral (non-polar) amino acid residues of naturally-occurring amino acids or natural or synthetic homologs thereof which are the same or different. Exemplary residues are those of Ala (alanine), Pro (proline), Ser (serine), Hyp (hydroxyproline), Thr (threonine), Cys (cysteine), Asn (asparagine), Gln (glutamine), and Tyr (tyrosine) dopa, all of which are neutral; and Lys (lysine), Arg (arginine), Glu (glutamic acid), and Asp (aspartic acid), all of which carry a charge. Preferably, $X_{aa}$ is Pro; more preferably, $X_{aa}$ is Pro and $X_{bb}$ is either Pro or Hyp, more preferably Hyp. Other synthetic or natural amino acids such as dopa or D-amino acids such as those corresponding to the above-mentioned naturally-occurring L-amino acids may also be used. For special purposes, Gly (glycine) may be replaced by another natural or synthetic amino acid, providing the overall intended biofunction of the mimic is not significantly thereby compromised. Replacement of Pro, Hyp, or exceptionally by amino acid residues having functional side chains, especially trifunctional residues, which promote adhesion of the mimic to cells, tissues, or fibrin is especially contemplated. Lys, Glu, and Asp are exemplary of such residues; other useful trifunctional amino acids for such uses are Ser, Thr, Tyr dopa, Cys, Arg, and His; as well as natural or synthetic homologs thereof. Glycosylated and sulfated residues may also be employed.

The consecutive triads forming the copolypeptide strands may be the same or different. As described above (J. Biol. Chem. 265, op. cit.) a triple helical secondary structure is preferred for cell adhesion to and spreading on the collagen mimic. Typically, the strands are interwoven or braided and referred to as "braid-like collagen mimics". As set forth in Formula A, each strand contains from about 3 to about 30 triads; 10 or fewer triads are generally preferred.

Each strand is preferably covalently linked at its C-terminal end to a template, optionally via a spacer as elaborated infra, to stabilize the triple helix; the linkage is conveniently an amide bond from reactive amino groups on the template. Any material which serves to stabilize the helix, possesses at least three functional groups, especially amino groups, for linking the three peptide strands to their spacers, and does not significantly compromise biofunctionality of the polypeptide strands either by its presence or linking reaction is useful in the practice of the invention. Known suitable templates include the 1,2,3-propanetricarboxylic acid, lysine-lysine dimer, and Kemp triacid template describe supra. The term "template" is used herein in its art-accepted meaning.

The optional spacer or leash spaces the amino acid residues of the polypeptide strands from the template to avoid steric hindrance of the functions of the residues. This spacer can be any bifunctional molecule which serves this purpose, is substantially biologically inert except for the reactive functional groups, and which can be covalently linked to the template and peptide strands via the functional groups without denaturing the biologically-active portions of the mimic. Many such spacers for spacing proteins from a support are known in the art, such as those used for spacing antibodies from an immobilizing support. Exemplary spacers for use in the collagen mimics include bifunctional linear $C_1$–$C_{10}$-alkylene groups having an active or activatable group at each end thereof, particularly one amino and one carboxyl group for forming amide bonds with the C-terminal ends of the strands and free amino groups of the template. Linear primary amino acid residues such as amino-hexanoyl are recommended.

In so-modified collagen mimics of the invention, a polymer is included to increase the molecular weight of the mimic, and/or to vary other properties of the mimic such as hydrophilicity, immunogenicity, and in vivo stability. As indicated in Formula A by "●", the polymer may be activated at one end thereof and grafted to the distal end of one or more of the peptide strands; to the distal end of the adhesive moiety; to the backbones of the strands or adhesive moiety; to the spacer; or to the template by covalent linkage of the activated groups to appropriate functional side chains or terminal groups of the mimic, especially amino or hydroxy groups. The polymer may also be activated at both ends for cross-linking of the mimic, particularly cross-linking of the peptide strands. Generally, the molecular weight of the polymer is from about 200 to 100,000 daltons, preferably at least about 1,000 daltons. Polyethylene glycol, especially monomethoxypolyethylene glycol, is a particularly suitable polymer for clinical use because of its known efficacies and safety as a protein modifier (supra). Polyvinyl alcohol, polyglutamic acid, polyaspartic acid, polylysine, or Pluronics™ polymers are also exemplary. The polymer may also be selected for its biodegradability, biocompatibility, benign reactivity with the mimic, and other properties as desired.

In so-modified collagen mimics of the invention, the adhesive moiety AM is selected to promote adhesiveness or cohesiveness of the mimic. The AM may be any moiety suitable for this purpose which may be covalently bonded to the template without significant denaturation of the product. If AM is to be present, the template must include at least one additional available functional group (in addition to the groups available for attaching each of the three polypeptide strands to the template) for attaching the template to the template. Adhesive moieties having adhesive properties which effectively cohere elements of the mimic to each other or adhere the mimic to a different material such as fibrin, skin or other tissue, or cells are contemplated. Particularly contemplated adhesive moieties are adhesive domains of certain proteins such as marine adhesive protein (MAP), or any other oligopeptide sequences, including $(X_{aa}-X_{bb}-Gly)_n$, having side chains which improve adhesiveness or cohesiveness of the mimic. Peptide sequences of fibronectin, laminin, elastin, or collagen having adhesive properties are also exemplary. Such peptide sequences are easily attached to the template for example by reaction of the C-terminal carboxyl groups of the sequence with a free amino group of the template. Coupling procedures for coupling selected moieties of the collagen mimic of the invention are generally known in the art.

The oligopeptide strand of the mimic are conveniently synthesized by solid phase synthesis techniques, solution techniques, or combinations thereof, as known in the art, using coupling procedures that allow the addition of N-protected amino acids having unprotected-OH side chains, such as Ser, Thr, Tyr, Hyp, and dopamine. They can also be prepared as fusion proteins or peptide fragments thereof from appropriate genetically-engineered expression vectors in suitable host cells. Either method provides artificial collagen free of endogenous mammalian pathogens.

2. Utilities

As noted, the artificial collagens of the invention are particularly useful as clinical materials for wound closing and healing. The material can, for example, be applied to skin lesions as a substitute for native collagen in any known surgical or clinical procedures. The artificial collagen may be used alone for such purposes, or in combination with other materials also used for wound closing and healing, especially fibrin or fibrinogen, to promote adhesion of these materials from the damaged site. Fibrin sealant compositions such as those described in U.S. patents, incorporating artificial collagens of the invention are particularly contemplated. Matrices of the artificial collagen are also very useful as supports for the growth and migration of skin cells, both in situ the wounds, and in the preparation of the artificial skin, as known for native collagen. In general, the artificial collagens of the invention are excellent substitutes for native mammalian collagen in all its applications, particularly clinical applications.

Artificial collagen according to the following formula I–IV are exemplary of these especially useful for wound closing and healing.

In a first embodiment of the invention, $X_{aa}$ and $X_{bb}$ in the oligopeptides $(X_{aa}-X_{bb}-Gly)-(X_{aa}-X_{bb}-Gly)_n-(X_{aa}-X_{bb}-Gly)$ preferably represent Pro and Hyp, respectively or represent Lys, Glu, Asp, Cys, Tyr, Ser, Thr, Arg, His, or dopa, in order to provide potential sites for non-covalent or covalent linkage with fibrin sealants and/or with neighboring cells and tissues, particularly skin cells and tissues $X_{aa}$ and $X_{bb}$ may be the same or different residues in each triad. Consecutive triads may be the same or different, and spacer and template are as described above. The products comprise structures shown in Formula I:

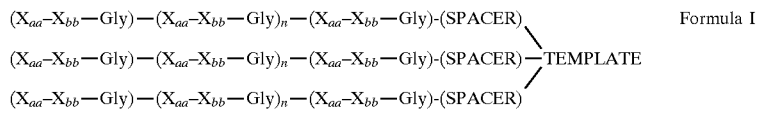

Formula I

In a second embodiment of the invention, a polymer, preferably PEG, is covalently linked to a reactive side chain of $X_{aa}$ and $X_{bb}$, or both, located in the same triad or in a different one. The molecular weight of the polymer is preferably between about 200 daltons and 100,000 daltons. The polymer can be activated at one end only or at both ends. In the latter case, cross-linking occurs between collagen mimic molecular weights up to several hundred thousand daltons are obtained. The products comprise modified oligopeptides of the Formula II:

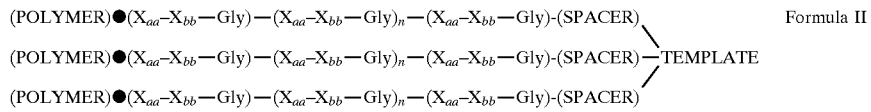

Formula II

In a third embodiment of the invention, an adhesive moiety designed as AM is added at the C-terminal end of the template. This moiety contains units that improve binding to fibrin sealants and/or to cells and tissues. This may be $(X_{aa}\text{-}X_{bb}\text{-}Gly)\text{-}(X_{aa}\text{-}X_{bb}\text{-}Gly)_n\text{-}(X_{aa}\text{-}X_{bb}\text{-}Gly)$, the sequence of units of marine adhesive proteins (MAPS) from molluscs *Mytilus edilus* or *Mytilus californianus*, or other pendants, including peptide chains, that provide additional binding sites for wound closing and healing purposes. The products comprise modified oligopeptides of the Formula III:

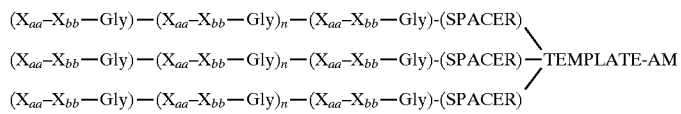

Formula III

In a fourth embodiment of the invention, a POLYMER, preferably PEG, is covalently linked to reactive chemical functions located in $(X_{aa}\text{-}X_{bb}\text{-}Gly)\text{-}(X_{aa}\text{-}X_{bb}\text{-}Gly)_n\text{-}(X_{aa}\text{-}X_{bb}\text{-}Gly)$ and/or in AM. The molecular weight of the polymer is typically between about 200 daltons and 100,000 daltons. The polymer may be activated at one end only, or at both ends. In the latter case, cross-linking occurs between collagen mimics, and molecular weights up to several hundred thousands daltons are obtained. The products comprise modified oligopeptides of the Formula IV:

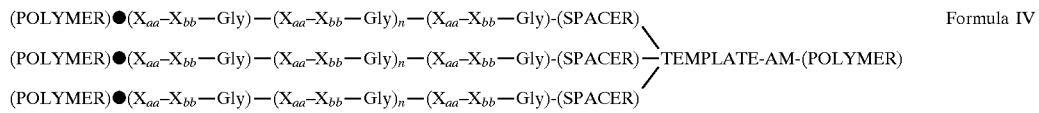

Formula IV

For most applications which involve the use of collagen mimics as additives to fibrin sealants for general purposes, Formula I with n between about 2 to 10 is employed, with a minimum of two reactive groups per chain. For applications which, for example, require a biomaterial mimic with strong adhesive properties, oligopeptides including the largest number possible of OH-containing side chains (Hyp, Ser, Thr, Dopa) are used as known in the art (J. Biomed. Mat. Res. 21:965, 1987). On the other hand, biomaterial with lowest immunogenicity possible does not contain charged residues as known in the art (J. Biol. Chem. 252:3578, 1977), or contains charged residues masked by PEG or other polymer, such as found in Formulae II and IV. The biomaterial can be as densely cross-linked as required, by for example, increasing intermolecular bridging between reactive side chains and using suitable bifunctional cross-linking agents such as activated PEG. Preferred triads $X_{aa}\text{-}X_{bb}\text{-}Gly$ include those wherein glycine is used as such, either $X_{aa}$ or $X_{bb}$ or both are proline, and $X_{aa}$ is proline and $X_{bb}$ is hydroxyproline. For applications which, for example, are dependent on the ability of the collagen mimic to adhere to and support migration of cells, the amino acid residues of the oligopeptide chains are preferably selected to promote the formation of ionic bridges between themselves and fibrinogen, and/or surrounding cells or tissues. In such a case, the insertion of a trifunctional amino acid such as lysine, glutamic or aspartic acid at position $X_{aa}$ of one or two triads is preferably selected.

EXAMPLES

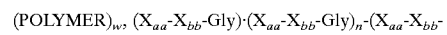

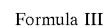

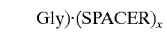

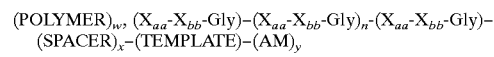

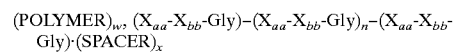

or

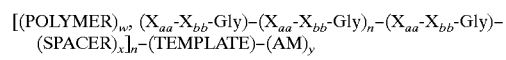

FORMULA A: General structure of synthetic collagen.
Synthesis of collagen-like peptides with amidated C-terminal In general, peptides corresponding to Formula A are assembled by the solid-phase synthesis (SPPS) method [R. B. Merrifield, J. Amer. Chem. Soc., 85, 2149–2154 (1963)]. Commercially available cross-linked (1%) copolystyrenedi-vinylbenzene resin, size 100–200 mesh, is used as a solid support. This resin is functionalized with benzhydrylamine (BHA) groups, with a degree of substitution varying between 0.25–0.75 mmol/gram. This degree of substitution is controlled by adjusting the temperature of the reaction and the stoechiometry of the reagents [P. G. Pietta & G. R. Marshall, J. Chem. Soc. D, 650–651 (1970)]. The value obtained can be measured by determining the nitrogen content, using the Kjeldahl method.

Synthetic collagens are generally prepared on a 0.5 mmol scale. The synthesis can be scaled up (several moles) as required. The peptide sequence is assembled from C- to N-terminal by repetitive, stepwise addition of N-α-protected amino acid derivatives, preferably Fmoc (fluorenyl-methyloxycarbonyl), using typical "base-acid" strategy. Boc (t-butyloxycarbonyl) derivatives and the "hard acid strategy" can also be used. The synthesis is carried out using an automatic peptide synthesizer (for example, Applied Biosystems Model 430A automatic synthesizer) for small scale (0.5 mmol), or a manual multiple synthesizer for larger scale.

Hydroxyproline is generally introduced in the growing peptide chain as the free hydroxyl Fmoc derivative. This is made possible by using benzotriazole-1-yl-oxy-tris-(dimethylamino)-phosphonium hexafluorophosphate (BOP) [B. Castro, J. R. Dormoy, G. Evin & C. Selve, Tet. Lett., 1219–1222 (1975)] or 2-(1 H-benzotriazole-1-yl-1,1,3,3-tetramethyluronium hexafluorophosphate (HBTU) [R. Knorr, A. Trzeciak, W. Bannwarth & D. Gillesen, Tet. Lett., 1927–1930 (1989)] as coupling agents. Other Fmoc derivatives of trifunctional amino acids have the following protecting groups on side chains: Lys(Boc), Tyr(Bu), Arg(Tos), Cys(Acm), Glu(OBu) and Asp(OBu). Removal of Fmoc protection is performed with 20% (v/v) piperidine: N,N-dimethylformamide (DMF).

Cleavage/side-chain deprotection of finished peptides is performed in liquid HF (0° C., 1 h) in the presence of anisole. Mercaptoethanol and/or thiocresol is added when sulfur-containing amino acids are present in the sequence. Following extraction from the resin and evaporation in vacuo (TFA or acetic acid extraction), the crude peptide is purified by reverse-phase HPLC on preparative columns containing 15–20 μm octadecylsilane ($C_{18}$) support, using appropriate linear 0.1% (v/v) TFA:acetonitrile gradients. The elution of peaks is monitored by reverse-phase analytical HPLC and the fractions containing the peptide are lyophilized. Characterizaton of the final peptides is carried out by analytical HPLC, amino acid analysis and MALDI-MS. Triple-helical conformation is determined by 2D-NMR [M. Goodman, Y. Feng, G. Melacini & J. P. Taulane, J. Amer. Chem. Soc., 118, 5156–5157 (1996)] and CD [M. G. Venugopal, J. A. M. Ramshaw, E. Braswell, D. Zhu & B. Brodsky, Biochemistry, 33, 7948–7956 (1994)].

EXAMPLE 1

Synthesis of [N-acetyl-(Pro-Hyp-Gly)$_{10}$Ahx]$_3$-Lys-Lys-amide

A quantity of two grams of benzhydrylamine resin (100–200 mesh, copolystyrene-divinylbenzene 1%, 0.5 mmol/g) bearing 1 mmol BHA hydrochloride is placed in a 100 ml fritted SPPS reactor. The resin is neutralized using a solution containing a 5 molar excess of N,N-diisopropylethylamine (DIEA) in DMF (20 ml). After filtration and washing of the resin (3 times 10 ml DMF), the synthesis proceeds according to the SPPS protocol summarized in Table 1. A mixture of HBTU (3 mmol), 1-hydroxybenzotriazole (HOBT) (3 mmol) and N-α-Fmoc-N-ε-Boc-Lys (3 mmol) dissolved in DMF (10 ml) is added and the slurry is agitated for 0.5 min using dry $N_2$. DIEA (3 mmol) is added and the coupling is carried out for 30 min under $N_2$ scrubbing. The reagents are drained to waste and the resin is washed 6 times with DMF. After checking for completion of coupling with the ninhydrin test, the synthesis is carried out by adding the second N-α-Fmoc-N-ε-Boc-Lys residue, according to the same schedule.

TABLE 1

Reaction schedule used for solid-phase peptide synthesis of collagen analogs

| Step | Reagent | Volume (ml/g resin) | Time (min) |
| --- | --- | --- | --- |
| Deprotection | Piperidine 20% (v/v) in DMF | 10 | 5 |
| Deprotection | Piperidine 20% (v/v) in DMF | 10 | 20 |
| Wash | DMF | 3 × 10 | 1 |
| Coupling | 3 equiv. Fmoc amino acid 3 equiv. HBTU/HOBT 3 equiv. DTEA in DMF | 10 | 30 |
| Wash | DMF | 3 × 10 | 1 |
| Wash | EtOH | 3 × 10 | 1 |
| Wash | DMF | 3 × 10 | 1 |

After checking for completion of coupling, the N-α-Fmoc protection is removed and Fmoc-aminohexanoic acid (Ahx) is added according to the schedule in Table 1, including the check for completion. The resin is washed 3 times with 20 ml $CH_2Cl_2$ and 20 ml of a 40% (v/v) solution of trifluoroacetic acid (TFA) in $CH_2Cl_2$ is added. The removal of Lys side chain Boc protecting groups proceeds within 30 min, followed by washing with $CH_2Cl_2$ (6×20 ml) and DMF (3×20 ml). The remaining two Ahx residues are then introduced at the next step as their Fmoc derivatives, according to Table 1, using again 3 equivalents per $NH_2$ site, plus 3 equivalents of DIEA. After checking for coupling completion, the synthesis proceeds with the stepwise addition of Fmoc-Gly, Fmoc-Hyp and Fmoc-Pro, according to Table 1, until the last Fmoc-Pro has been introduced, which corresponds to the assembly of ten complete (Pro-Hyp-Gly) triads. After removal of Fmoc protection, the peptide is acetylated using 50 equivalents of acetic anhydride in DMF. After washing with DMF (3 times), $CH_2Cl_2$ (3 times) and ethanol (3 times), the resin is dried for 1 h in vacuo in a dessicator at 50° C. The resin-peptide is placed in the reactor (100 ml) of a Kel-F/Teflon HF ramp (Protein Research Foundation, Osaka, Japan) and the peptide is cleaved off the resin using liquid HF (10 ml/g resin-peptide) at 0° C. for 1 h, in the presence of anisole (1 ml/g). After 1 h, HF is rapidly evaporated in vacuo. The peptide is extracted from the resin using neat TFA (20 ml/g); the resin is washed with TFA (10 ml) and the TFA is evaporated in vacuo. The syrupy residue is triturated with anhydrous ethyl ether to obtain a white powder which is rapidly filtered on a fritted funnel and dried in vacuo in a dessicator in the presence of KOH pellets.

The crude peptide (ca. 2.5 g) is dissolved in 50 ml of aqueous dilute TFA (0.1 % v/v). The solution is filtered and injected onto a 1×30 cm stainless steel HPLC (high-performance liquid chromatography) column containing octadecylsilica reverse-phase support. The peptide is eluted using a linear gradient of 0.1% TFA:acetonitrile. The fractions containing the peptide are detected online at 230 nm and collected. Acetonitrile is evaporated in vacuo using a rotary evaporator and the aqueous solution is lyophilized. The purified peptide is characterized by amino acid analysis (Pro:Gly:Lys) and MALD1 mass spectrometry. Triple-helical conformation is determined by 2D-NMR [M. Goodman, Y. Feng, G. Melacini & J. P. Taulane, J. Amer. Chem. Soc., 118, 5156–5157 (1996)] and circular dichroism [M. G Venugopal, J. A. M. Ramshaw, E. Braswell, D. Zhu & B. Brodsky, Biochemistry, 33, 7948–7956 (1994)].

Synthetic collagens modified with polyethylene glycol

Besides being a useful agent for precipitating proteins, highly hydrophilic polyethylene glycol (PEG) has recently found several applications in the field of biomaterials. It is widely available in a large number of molecular weight fractions at a relatively cheap price. PEG and its homolog, the block copolymer PEG/PPG/PEG, distributed under the name Pluronics by BASF, can be readily functionalized and activated with a number of chemical functions. Bissuccinate or succinate esters of PEG [M. Z. Atassi & T. Manshouri, J. Protein Chem., 10, 623–627 (1991)] can be prepared readily, using PEG or PEG-monomethyl ether (methoxy-PEG), respectively. The carboxyl(s) group(s) can then be activated to a succinimide ester by means of N-hydroxysuccinimide PEG bis-succinimide esters can be used as cross-linking agent to generate controlled pore size material, while methoxy-PEG succinimide ester can form pendants of defined molecular weight. PEG carbamate [T. M. Allen, C. Hansen, F. Martin, C. Redemann & A. Yau-Young, Biochim. Biophys. Acta, 1066, 29–36 (1991)] is another useful form of activated PEG; as previously, it can be used to prepare mono- or bis-activated PEGs.

Commercial PEG and methoxy-PEG are available from Aldrich and other chemical suppliers, with molecular weights ranging from 200 to 10,000 daltons. The choice of molecular weight is guided by the biomechanical properties required for a given application. Covalent attachment of PEG to proteins was shown to decrease their antigenicity and immunogenicity [A. Abuchowski, J. R. McCoy, N. C. Palczuk, T. Van Es & F. F. Davis, J. Biol. Chem., 252, 3582–3586 (1977)] and to extend their circulation half-life [T. M. Allen, C. Hansen, F. Martin, C. Redemann & A. Yau-Young, Biochim. Biophys. Acta, 1066, 29–36 (1991)]. Also, the use of PEG-protein conjugates has been approved by US FDA for use in humans in 1990 [R. Pool, Science, 248, 305 (1990)].

EXAMPLE 2

Synthesis of [PEG3000-(Pro-Hyp-Gly)$_{10}$Ahx]$^3$-Lys-Lys-amide 300 g (0.1 mole) of commercial monomethoxy-polyethylene glycol (Aldrich) with an average molecular weight in the range of 3000 daltons is treated with succinic anhydride (50 g, 0.5 mole), according to Atassi et al. [M. Z. Atassi & T. Manshouri, J. Protein Chem., 10, 623–627 (1991)], to yield monomethoxy-PEG3000-monosuccinate. The carboxyl group is then activated by reacting the monosuccinate (0.1 mole) with N-hydroxysuccinimide (23 g, 0.2 mole) and N,N-dicyclolhexylcarbodiimide (DCC) (0.2 mole, 41 g) in $CH_2Cl_2$ at 0° C. overnight. After filtering dicyclohexylurea, $CH_2Cl_2$ is evaporated in vacuo and the residue precipitated in ethyl ether. After filtration and generous washing with ether, monomethoxy-polyethylene glycol succinimide ester (PEG-NHS) is redissolved in a minimum volume of $CH_2Cl_2$, precipitated in ether, washed with ether and dried in vacuo.

The same procedures described in Example 1 are used to assemble the peptide up to the N-terminal Pro residue, with the exception that the N-terminal imino group is not acetylated. The peptide is cleaved off the resin using liquid HF, purified and characterized as in Example 1. The peptide (3 g, ca. 0.1 mmole) is dissolved in amine-free DMF (10 ml) in a round-bottom flask and the solution is cooled to 0° C. PEG-NHS (10 g, ca. 0–3 mmol) dissolved in 10 ml DMF is then added and the reaction is carried out for 24 h in a cold room (4° C.). DMF is evaporated in vacuo and the residue is triturated with ether. The white solid is washed with ether, filtered, and redissolved in a minimum volume of DMF. An excess of ether is added to the solution and the precipitate is treated and characterized as described above.

Synthetic collagens modified with polyethylene glycol that contain a functional peptide chain in C-terminal In the invention, AM in Formula A represents a peptide sequence that can be used to confer desired properties to synthetic collagen. Such properties might be extra reactive sites for PEG attachment, but also extra functional groups such as hydroxyls that contribute to increase the viscosity of formulations. AM represents a new concept for the preparation of chimeric synthetic collagens that can be used as hybrid scaffolds in the process of wound closing and healing.

Several peptide sequences known to be involved in cell and tissue adhesion described during the past several years can be used as AM to prepare chimeric synthetic collagens. Examples of such sequences are marine adhesive protein [J. H. Waite, J. Biol. Chem., 258, 2911–2915 (1983); J. H. Waite U.S. Pat. No. 4,585,585 (1986); J. H. Waite, Int. J. Adhesion Adhesives, 7, 9–14 (1987)], YIGSR- and RGD-containing peptides [M. V. Agrez, R. C. Bates, A. W. Boyd & G. F. Burns, Cell Regul., 2, 1035–1044 (1991) from the sequence of fibronectin, REDV- and IKVAV-containing sequences from laminin [R. F Service, Science, 270, 230–232 (1995); M. Nomizu, A. Utani, N. Shiraishi. Y. Yamada & P. P. Roller, Int J. Pept. Prot. Res., 40, 72–79 (1992)] and sequences from tropoelastin such as VGVAPG and PGAIPG [L. E. Grosso & M. Scott, Matrix, 13, 157–164 (1993)]. For instance, it was shown recently that RGD-containing peptides can promote fibroblast stretching on collagen and induce collagen binding by integrins or specifically attract endothelial cells. Such properties are highly desirable in order to obtain specific and performing fibrin sealant formulations.

Furthermore, AMs can be used to introduce chemically reactive sites and/or photoreactive sites. Such sites will react with heterobifunctional activated reagents of various chain lengths, in order to design high molecular weight, tridimensional networks of SCM with a controlled degree of cross-linking. Such reactive sites are Lys, Glu, Asp, Cys and photoreactive analogs of Phe [E. H. F. Escher, T. M. D. Nguyen, H. Robert, D. Regoli & S. A. St-Pierre, J. Med. Chem., 21, 860–864 (1978); F. S. Tjoeng, W. Staines, S. A. St-Pierre & R. S. Hodges, Biochim. Biophys. Acta, 490, 489–496 (1977)].

EXAMPLE 3

Synthesis of [PEG3000-(Pro-Hyp-Gly)$_{10}$ Ahx]$^3$-Lys-Lys-(Arg-Gy-Asp)$_3$ amide The same procedures described in Example 1 are used to assemble the peptide, with the exception that Fmoc-Asp-β (Bzl) is attached to the BHA resin. The next residues to be introduced are, in sequence, Fmoc-Gly and N-α-Fmoc-N-g-Tos-Arg. This sequence is repeated twice more, according to Table 1. Thereafer, N-α-Fmoc-N-εBoc-Lys is introduced and the synthesis proceeds, in sequence, with the addition of the second N-α-Fmoc-N-ε-Boc-Lys, Fmoc-Ahx, followed, by the 10 (Pro-Hyp-Gly) triads. Following the usual workup described in Example 1, PEG3000 is introduced as its succinimide ester, as described in Example 2. The resulting chimeric peptide is isolated, purified and characterized as described in Example 2.

What is claimed is:

1. Artificial collagen molecule comprising a water-soluble, stabilized ordered copolypeptide triple-helix characterized by three polypeptide strands of amino acid triads, each strand covalently linked via the C-terminal end thereof to a common template of the formula:

(POLYMER)$_w$●{[(X$_{aa}$-X$_{bb}$-Gly)-(X$_{aa}$-X$_{bb}$-Gly)$_n$-(X$_{aa}$-X$_{bb}$-Gly)-(SPACER)$_x$]$_3$-(TEMPLATE)-(AM)$_y$} wherein X$_{aa}$ and X$_{bb}$ independently of each other are each a hydrophilic or neutral residue of a naturally-occurring amino acid or homolog thereof;

TEMPLATE is a stabilizing moiety containing at least three functional groups each reacted with the C-terminal end of one polypeptide strand and capable of stabilizing the triple-helix;

POLYMER is a polymer from about 200 to 100,000 daltons covalently linked at at least one end thereof to functional amino acid residue side chains present in the triple helix or in AM, or at the N-terminal end of each strand of the triple helix;

AM is a adhesive moiety for promoting cohesiveness of the molecule or adhesiveness of the molecule or both;

SPACER is a bifunctional linear molecule covalently linked to the C-terminal end of each polypeptide strand and to the template;

n is from 1 to 28;

x and y are each independently one or zero; and w is from 0 to 30;

each triad is the same or different; and at least one of x, y, or w is one or more.

2. Artificial collagen according to claim 1, wherein w is zero, and y is one.

3. Artificial collagen according to claim 1, wherein y is zero and w is one or more.

4. Artificial collagen according to claim 1, wherein y is 1 and w is one or more.

5. Artificial collagen according to claim 1, wherein x is one.

6. Artificial collagen according to claim 1, wherein the strands are substantially identical.

7. Artificial collagen according to claim 1, wherein the strands are braided.

8. Artificial collagen according to claim 1, wherein n is from 1–8.

9. Artificial collagen according to claim 1, wherein the functional groups of TEMPLATE are free amino groups.

10. Artificial collagen according to claim 1, wherein x is one and SPACER is a bifunctional linear C$_1$–C$_{10}$-alkylene group.

11. Artificial collagen according to claim 10, wherein SPACER is NH$_2$–(CH$_2$)$_m$–COOH, and wherein n is from 1 to 10.

12. Artificial collagen according to claim 1, wherein POLYMER is covalently linked at each end thereof to the molecule to cross-link the polypeptide strands.

13. Artificial collagen according to claim 1, wherein in each triad, X$_{aa}$ and X$_{bb}$ independently of each other are Pro, Hyp, Lys, Glu, Asp, Cys, Tyr, Ser, Thr, Arg, His or dopa.

14. Artificial collagen according to claim 13, wherein X$_{aa}$ and X$_{bb}$ independently of each other are Pro, Hyp, Lys, Glu, or Asp.

15. Artificial collagen according to claim 13, wherein X$_{aa}$ and X$_{bb}$ independently of each other are Pro or Hyp.

16. Artificial collagen according to claim 1, wherein TEMPLATE is 1,2,3-propanetricarboxylic acid, a lysyl-lysine dipeptide, or (cis,cis-1,3,5-trimethylcyclohexane-1,3,5-tricarboxylic acid).

17. Artificial collagen according to claim 1, wherein w is one or more and POLYMER is polyethylene glycol.

18. Artificial collagen according to claim 1, wherein w is one or more and POLYMER is either of Pluronics™, polyvinyl alcohol, polyglutamic acid, polyaspartic acid or polylysine.

19. Artificial collagen according to claim 12, wherein X$_{aa}$ and X$_{bb}$ independently of each other are Pro, Hyp, Lys, Glu, Asp, Cys, Tyr, Ser, Thr, Arg, His or dopa.

20. Artificial collagen according to claim 1, wherein y is one and AM is a peptide sequence of marine adhesive protein.

21. Artificial collagen according to claim 1, wherein y is one and AM is a peptide sequence of either fibronectin, laminin, elastin or collagen.

22. Artificial collagen according to claim 1, wherein x is one and SPACER is covalently linked to the C-terminal end of each polypeptide strand via an amide bond.

23. Artificial collagen according to claim 22, wherein SPACER is aminohexanoyl.

24. A tissue sealant composition comprising artificial collagen according to claim 1.

25. The composition of claim 24, further comprising fibrinogen.

26. Artificial skin comprising a skin cell cultured on the artificial collagen of claim 1.

27. A method for repairing damaged skin tissue comprising contacting the damaged site with the artificial collagen of claim 1.

28. In a clinical procedure for repairing tissue damage wherein native collagen is employed to promote healing, the improvement comprising employing the artificial collagen of claim 1 instead of at least a portion of the native collagen.

29. A collagen matrix comprising at least two cross-linked artificial collagen molecules according to claim 1.

30. Artificial collagen according to claim 14, wherein either X$_{aa}$ or X$_{bb}$ or both are Pro.

31. Artificial collagen according to claim 30, wherein X$_{aa}$ is Pro and X$_{bb}$ is Hyp.

32. Artificial collagen of claim 14, wherein in at least one triad of each polypeptide strand, X$_{aa}$ is Lys, Glu, or Asp.

33. Artificial collagen of claim 32, wherein in the triads not containing Lys, Glu, or Asp, X$_{aa}$ is Pro.

34. Artificial collagen according to claim 1, wherein w and x are each zero and y is one, of the formula:

[(X$_{aa}$-X$_{bb}$-Gly)-(X$_{aa}$-X$_{bb}$-Gly)$_n$-(X$_{aa}$-X$_{bb}$-Gly)]$_3$-[TEMPLATE] AM.

35. Artificial collagen according to claim 34, wherein in each triad X$_{aa}$ is Pro, and X$_{bb}$ is Hyp, n is 2, and the peptide strands are substantially identical.

* * * * *